United States Patent [19]

Nakamura et al.

[11] Patent Number: 5,321,177
[45] Date of Patent: Jun. 14, 1994

[54] PROCESS FOR THE VAPOR-PHASE THERMAL CRACKING OF DICYCLOPENTADIENE AND A PROCESS FOR THE MANUFACTURE OF HIGH PURITY DICYCLOPENTADIENE

[75] Inventors: Takao Nakamura, Ichihara; Masaru Kawakita, Chiba; Katsumi Minomiya, Ichihara, all of Japan

[73] Assignee: Maruzen Petrochemical Co., Ltd., Tokyo, Japan

[21] Appl. No.: 869,612

[22] Filed: Apr. 16, 1992

[30] Foreign Application Priority Data

Apr. 18, 1991 [JP] Japan .................................. 3-114088
Feb. 18, 1992 [JP] Japan .................................. 4-069134

[51] Int. Cl.$^5$ ...................... C07C 5/31; C07C 403/00; C07C 7/148
[52] U.S. Cl. .................................... 585/318; 585/315; 585/354; 585/362; 585/832; 203/30
[58] Field of Search ............... 585/354, 362, 832, 315, 585/318; 203/30

[56] References Cited

U.S. PATENT DOCUMENTS

| | | | |
|---|---|---|---|
| 2,349,047 | 5/1944 | Lycan et al. | 585/354 |
| 2,453,044 | 11/1948 | Staff | 260/666 |
| 2,582,920 | 1/1952 | Businger et al. | 260/666 |
| 2,831,904 | 4/1958 | Kreps | 260/666 |
| 3,529,027 | 9/1970 | Helmke, Jr. et al. | 260/666 |
| 3,676,509 | 7/1972 | Heiman | 260/666 |

FOREIGN PATENT DOCUMENTS 51-29145 8/1976 Japan .

Primary Examiner—Anthony McFarlane
Assistant Examiner—Nhat D. Phan
Attorney, Agent, or Firm—Melvin I. Stoltz

[57] ABSTRACT

Recently, as a process for manufacturing cyclopentadiene resin-shaped articles, an attention has been given to reaction injection molding (RIM). To conduct RIM, it is necessary to use high purity dicyclopentadiene (DCPD) as the raw material. Vapor-phase thermal cracking of DCPD is usually used as a step of process for manufacturing high purity DCPD. Hithertofore, when conducting thermal cracking of DCPD, coke formation within cracking tubes is the most serious and troublesome problem. A vapor-phase thermal cracking process for resolving the problem by a very simple procedure is described herein. Further, a process for manufacturing high purity DCPD suitable as a raw material for use in RIM utilizing the vapor-phase thermal cracking process just mentioned above is also described.

6 Claims, 3 Drawing Sheets

PROCESS FOR THE VAPOR-PHASE THERMAL CRACKING OF DICYCLOPENTADIENE AND A PROCESS FOR THE MANUFACTURE OF HIGH PURITY DICYCLOPENTADIENE

BACKGROUND OF THE INVENTION

1. Field of the Invention

The present invention relates to a vapor-phase thermal cracking process of dicyclopentadiene which can achieve a superior cracking rate and can be operated in a stable manner for a long period of time, and to a simple and industrial process for manufacturing high purity dicyclopentadine suitable as a raw material for the reaction injection molding (hereinafter called RIM).

2. Description of the Prior Art

Hithertofore, dicyclopentadiene have been used, as its industrial usage, as a third component of ethylene-propylene rubbers, as a raw material for unsaturated polyesters, and the like. Generally, dicyclopentadiene have been manufactured by a process of dimerizing $C_5$ fractions by-produced in thermal cracking of petroleums, typified by naphtha, and the like. In this instance, since the products contained many impurities by-produced in the dimerization reaction, such as cyclic codimers of cyclopentadiene with butadiene, isoprene, piperylene, etc. (vinylnorbornene, isopropenylnorbornene, propenylnorbornene, etc., hereinafter called codimers) and polymerization addition reaction products, such as tricyclopentadiene, and the like, and, further, oxides and the like of these compounds, their purity was about 70-95% by weight (hereinafter called crude dicyclopentadiene).

In recent years, an attention has been given, as a novel usage of dicyclopentadiene, to a method for the manufacture of molded articles of polycyclopentadiene resins with a crosslinked structure by RIM in which the polymerization reaction and the injection molding proceed simultaneously by the use of a ring opening polymerization by a metathesis catalyst comprising a tungsten compound or a molybdenum compound and an organo-aluminum compound.

However, if the crude dicyclopentadiene is used for the RIM the metathesis catalyst is deactivated by impurities such as those mentioned above, failing to induce a sufficient polymerization activity of the catalyst. Even if the crude dicyclopentadiene can be polymerized, the articles made therefrom may be inadequately molded or their physical strength may be reduced. Thus, studies concerning processes for the improving the purity have been ongoing.

Among one of the processes, there is a process for removing the impurities by repeated distillation. The process, however, is not economical due to the requirement of a distillation column with a very high number of theoretical plates because of the proximity in boiling points of the impurities and dicyclopentadiene, the necessity of regulating the recovery rate of dicyclopentadiene at a low level, and the like.

Because of this, a process for the manufacture of high purity dicyclopentadiene by the thermal cracking and redimerization of crude dicyclopentadiene has been proposed. Since the rate of thermal cracking reaction is greater in dicyclopentadiene than in codimer, cyclopentadiene is selectively obtained by the thermal cracking when the both are present together. Furthermore, since the rate of the thermal dimerization of cyclopentadiene overwhelmingly predominates that of the codimerization reaction of cyclopentadiene and other diolefins, the selectivity to dicyclopentadiene is even higher. This process utilizes these differences in the reaction rates.

A process for cracking dicyclopentadiene in the liquid phase in the presence of high boiling point hydrocarbon oils was proposed as a process for the thermal cracking of dicyclopentadiene (U.S. Pat. No. 2,831,904). The process, however, is complicated and uneconomical; cracking at a relatively low temperature, i.e., 200°-300° C., affords only a low yield of cyclopentadiene, and a large amount of polymers, such as dicyclopentadiene and the like, accumulate in hydrocarbon oils, which may clog tubes in the apparatus, leaving a problem of exhaust oil treatments, and the like.

Furthermore, a process for the vapor-phase cracking of dicyclopentadiene at a higher temperature in the presence of gaseous diluents such as steam, nitrogen gas, or the like, in order to promote its rate of cracking, was proposed (U.S. Pat. No. 2,582,920). The same problem of clogging the system by the accumulation of carbonized materials in the thermal cracking unit during a continuous operation in a short period of time was indicated concerning with this process. As a method of overcoming this problem, a cracking process was proposed, in which a feed is introduced after the removal of polymers and tar-like materials, which are the cause of the clogging of tubes, by contacting the feed with super-heated steam, and the cracking is carried out not by the external heating but by the use of heated steam itself (Japanese Patent Publication No. Sho 51 (1976)-29145). The process requires complicated pretreatment steps; it is difficult for the process to produce, by itself, high purity dicyclopentadiene suitable as a raw material for RIM in an industrial scale and in a stable manner.

SUMMARY OF THE INVENTION

The present invention resolves the aforementioned drawbacks in prior art processes; its object is to ensure a stable, long-term continuous operation by regulating the direction of fluid-flow in the cracking apparatus, without requiring a complicated pretreatment step, and to provide, inexpensively and in an industrial scale, high purity dicyclopentadiene suitable for use as a raw material of RIM.

The present inventors have undertaken earnest studies in order to overcome the aforementioned drawbacks in the vapor-phase cracking processes, and found a thermal cracking process for efficiently producing high purity dicyclopentadiene from crude dicyclopentadiene by introducing specific cracking conditions to the vapor-phase thermal cracking step, ensuring a long-term operation without requiring complicated procedures. Furthermore, the present inventors combined the cracking step using the process mentioned above with dimerization steps, distillation steps, and the like, thus succeeded in establishing a process for manufacturing high purity dicyclopentadiene, and completed the present invention.

Accordingly, the gist of the present invention resides, firstly, a process for the vapor-phase thermal cracking of dicyclopentadiene characterized in that a mixture of a dicyclopentadiene fraction with a concentration of 70% by weight or more and water and/or steam is continuously introduced to an externally heated cracking tube to effect vapor-phase thermal cracking at a temperature within a range of 250°-450° C. to produce cyclopentadiene, wherein the direction of flow of the mixture passing through said cracking tube is constantly maintained downward; and secondly, a process for the manufacture of high purity dicyclopentadiene characterized by comprising [A] a cyclopentadiene dimerization step in which a $C_5$ fraction by-produced in thermal cracking of petroleums, as a feedstock, is heated, [B] a dicyclopentadiene concentration step in which unreacted $C_5$ components are removed from the effluent of step [A] to obtain crude dicyclopentadiene with the concentration of 70% by weight or more, [C] a vapor-phase thermal cracking step in which the mixture of said crude dicyclopentadiene and water and/or steam is thermally cracked in a cracking tube or tubes at a temperature within a range of 250°–450° C., [D] a liquefaction-separation step in which water and heavy components are separated and removed from the effluent of step [C] and then liquefied cyclopentadiene is recovered, [E] a re-dimerization step of cyclopentadiene obtained from step [D], [F] a light component removing step in which a light component is removed from the effluent of step [E], and [G] a distillation step for the purification of dicyclopentadiene in which the effluent of step [F] is fractionated, wherein the direction of flow of said mixture passing through said cracking tube is constantly maintained downward, and a heavy fraction obtained as bottom fraction of step [G] is recycled to said step [C] or an upstream side thereof.

DETAILED DESCRIPTION OF THE INVENTION

Figure 1:
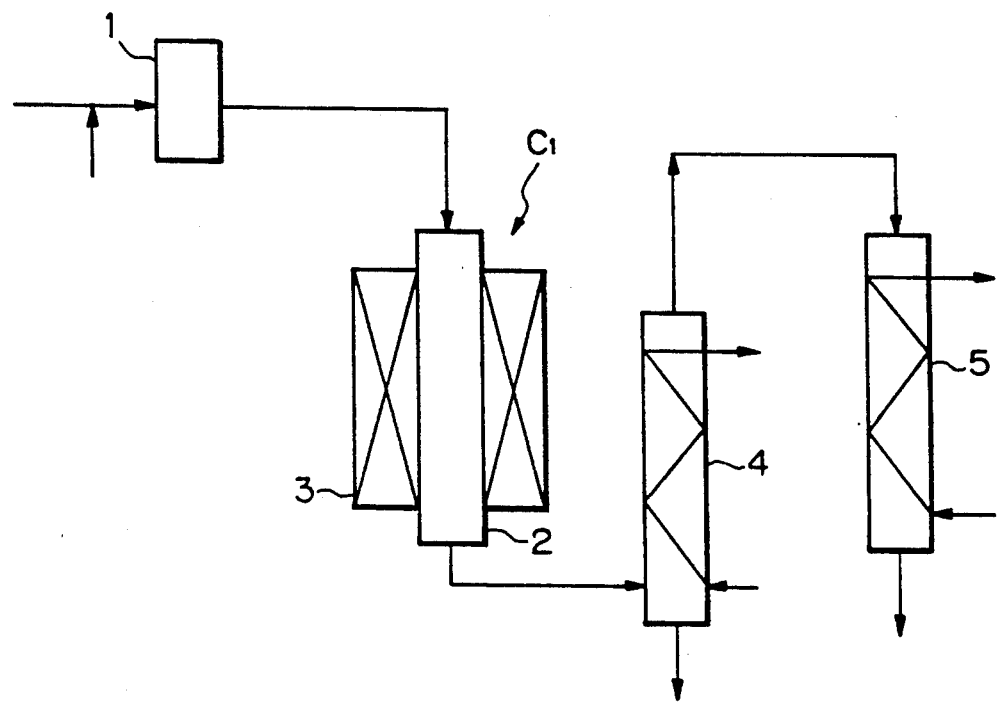
FIG. 1 shows an example of vapor-phase thermal cracking step of dicyclopentadiene and liquefaction separation step of cyclopentadiene according to the present invention.

In more detail, $C_5$ fractions by-produced in thermal cracking of petroleums, typified by naphtha, and the like, which are used as a raw material in the present invention, generally contain about 10–20% by weight of cyclopentadiene and dicyclopentadiene in a total of the both compounds and have a composition shown, for example, in Table 1 given hereinafter.

The fraction with such a composition is firstly fed to the dimerization step [A] for converting cyclopentadiene into dicyclopentadiene. The dimerization reaction conditions are determined depending on the content of cyclopentadiene, and the like, and usually the reaction is carried out at 80°–110° C. for 2–6 hours. The operation is carried out under optimum conditions to achieve the production rate of dicyclopentadiene as high as possible and the production rate of codimer of cyclopentadiene and diolefin, and the like as low as possible.

As a $C_5$ fraction, a so-called spent $C_5$ fraction which is a $C_5$ fraction from which useful isoprene has been extracted, can be used in the same way. Such a fraction, however, has already been subjected to a treatment similar to the treatment in the dimerization step when isoprene is extracted. It can thus be deemed to have been subjected to the treatment of step [A], so that the step [A] can be omitted in such a case.

The $C_5$ fraction passed through the dimerization step [A] is, then, sent to the next dicyclopentadiene concentration step [B], wherein a procedure is effected to remove unreacted materials by distillation and to increase the dicycloentadiene content to 70% by weight or more. Since the unreacted materials have a boiling point of 10°–60° C. and dicyclopentadiene has a boiling point of 170° C., the distillation procedure can easily separate one from the other. In general, a major part of unreacted materials is removed by an atmospheric distillation procedure, and the remaining part is removed by a successive vacuum distillation procedure. It is, however, possible to omit the vacuum distillation procedure if dicyclopentadiene with a concentration of 70% by weight or more can be obtained by the atmospheric distillation alone. Since dicyclopentadiene gradually decomposes into cyclopentadiene when heated to a temperature of above 120° C., conditions under which the column bottom temperature is controlled below 120° C. is usually selected in order to suppress the thermal cracking of dicyclopentadiene and to improve the recovery rate of dicyclopentadiene. The unreacted materials are recovered from the top of the column and concentrated dicyclopentadiene (crude dicyclopentadiene) is recovered from the bottom by the distillation procedure.

The content of dicyclopentadiene in the crude dicyclopentadiene is preferably 70% by weight or more, and more preferably 80–90% by weight. The most of the impurities contained in the crude dicyclopentadiene is occupied by codimers which is reaction products of cyclopentadiene and diolefins (vinylnorbornene, isopropenylnorbornene, propenylnorbornene, etc.), heavy components such as tricyclopentadiene, and the like, with a slight amount of light components such as piperylene, cyclopentene, n-hexane, and the like. A concentration of dicyclopentadiene of less than 70% by weight is not desirable, because dicyclopentadiene of such a low concentration entails contamination of a large amount of light components as impurities in cyclopentadiene which is the main cracking product of the next vapor-phase thermal cracking step [C], thus resulting in difficulties in obtaining high purity dicyclopentadiene which is the target product of the present invention. A concentration of dicyclopentadiene of more than 90% by weight in this concentration step [8] is also not desirable, because manufacturing dicyclopentadiene of such a high concentration may require, in general, distilling out of dicyclopentadiene from the top of the column together with light fractions, thus remarkably decreasing the recovery rate of dicyclopentadiene.

The light components removed from the concentration step [8] contain useful components such as isoprene, piperylene, and the like so that it can be used as a raw material for manufacturing petroleum resins or the like.

Next, the crude dicyclopentadiene is fed to the vapor-phase thermal cracking step [C] after mixed with a suitable amount of water and/or steam. The ratio of mixing of water and/or steam for 100 parts by weight of the crude dicyclopentadiene is preferably 5–230 parts by weight. If the amount of water and/or steam is less than 5 parts by weight per 100 parts by weight of crude dicyclopentadiene, inside of cracking tubes becomes heavily foul with polymers of dicyclopentadiene and the like, which may lead to clogging of the tubes in a short period of time. On the other hand, the amount of water and/or steam more than 230 parts by weight per 100 parts by weight of the crude dicyclopentadiene results in requirement of an excessive heat supply in the cracking unit and is thus uneconomical.

In this instance, the mixture of the crude dicyclopentadiene and water and/or steam may be directly fed to the vapor-phase thermal cracking step [C] or may be fed to the step [C] after distillation in the presence of water and/or steam. The present inventors also found that if the above mixture was distilled in advance in the presence of water and/or steam, and a fraction distilled at a temperature of below 120° C. as converted into the atmospheric pressure and comprising water and dicyclopentadiene as major components, was fed to the vapor-phase thermal cracking step [C], a more stable, long-term continuous operation of the vapor-phase thermal cracking step [C] was possible as compared with the case where said mixture, i.e., said crude dicyclopentadiene and water and/or steam, was directly introduced to the vapor-phase thermal cracking step [C]. Since the crude dicyclopentadiene which is the raw material to be fed to this step has already been processed by the distillation to remove light components therefrom, the fractions distilled out at a temperature below 120° C. as converted into the atmospheric pressure in this step do not essentially contain such light components as, for example, those having a boiling point of below 30° C. under the atmospheric pressure. Said distillation can be carried out generally by a simple distillation column. Since dicyclopentadiene and water provide an azeotropic mixture which can be distilled under the atmospheric pressure at 98° C. (compositions: dicyclopentadiene/water=32 wt/68 wt) and steam distillation is also applicable to dicyclopentadiene, almost all dicyclopentadiene is distilled out from the top of the distillation column by azeotropic or steam distillation, and heavy components (substances causing cracking tubes to clog in the vapor-phase thermal cracking step [C] of the present invention) are easily separated and removed at a low temperature from the bottom of the distillation column. Hithertofore, the heavy components cannot easily be separated from dicyclopentadiene at such a low temperature. Accordingly, the mixing ratio of 50–230 parts by weight of water and/or steam for 100 parts by weight of crude dicyclopentadiene is preferable when azeotropic or steam distillation is carried out. The mixing ratio of water and/or steam below 50 parts by weight per 100 parts by weight of crude dicyclopentadiene not only lowers the recovery rate of dicyclopentadiene but also raises the boiling temperature, causing heavy components to accompany. On the other hand, the mixing ratio of greater than 230 parts by weight is not desirable, because a large amount of heat supply is necessary for the distillation and the vapor-phase thermal cracking step. Furthermore, fractions distilled at a temperature above 120° C. as converted into the atmospheric pressure accompany heavy components and the like which readily polymerize at a high temperature. Such fractions therefore tend to heavily foul the inside of cracking tubes and clog the tubes in a short period of time. Therefore, a preferable mixing ratio of water and/or steam and crude dicyclopentadiene is to provide a distillate having dicyclopentadiene/water weight ratio between 3/7 and 7/3 which is distillable at a temperature of below 120° C. under the atmospheric pressure. The azeotropic or steam distillation can be conducted under any desired pressure, but preferably can be conducted under about the atmospheric pressure from the view points of easy separation and sufficient recovery of dicyclopentadiene and process economy.

The raw material mixture of crude dicyclopentadiene and water and/or steam may be introduced into the vapor-phase thermal cracking step [C] as liquid, liquid/-gas mixture, or gas. Usually, it is heated in advance by a preheater before the introduction and introduced as a liquid/gas mixture or, preferably, as a gas. When azeotropic or steam distillation is carried out, introduction as a gas is clearly preferable from the aspects of heat economy as well as investment cost of the apparatuses and its operation.

It is to be noted that the limitation of "crude dicyclopentadiene with concentration of 70% by weight or more" is meaningful relative to not only for improving the purity of target dicyclopentadiene but also for the operation of vapor-phase thermal cracking per se. Dicyclopentadiene is somewhat unstable material and has a tendency to form cokes or resinous materials when subjected to a thermal cracking operation. When crude dicyclopentadiene served to a thermal cracking operation contains a large amount of stable components such as paraffins, the crude dicyclopentadiene can easily be cracked safely even by conventional processes, because such stable components act as diluents. When crude dicyclopentadiene served to thermal cracking operation contains a large amount of very unstable components such as butadiene, isoprene and the like, the crude dicyclopentadiene may be difficult to thermally crack smoothly even by the use of the thermal cracking process of the present invention.

The apparatus for the cracking of dicyclopentadiene according to the present invention may be a straight cracking tube made of a metal which is aligned vertically or with a slope and with an exit positioned lower than the inlet side, or a spiral metallic tube vertically positioned. Alternatively, the cracking tube may be a tube bending right and left or a tube waving right and left arranged vertically or with a slope and with an exit provided at a position lower than the inlet side. A structure of a tube bending up-and-down or a tube waving up-and-down cannot be used as a cracking tube for use in the process of the present invention. Heating may be made by means of heating with a high temperature combustion gas obtained from a combustion furnace, heating by an electric furnace, or indirect heating by a heat transfer oil, a molten salt, or high pressure or superheated steam, and effected from outside of the tube. Cracking heat is continuously supplied so as to maintain the cracking temperature at 250°–450° C.

It is essential that flow of the fluid in the cracking tube should be constantly kept downward. Introduction of the above-mentioned mixed raw material is made from the upper side inlet of the cracking tube and removal of cracked gases from the exit in the lower side of the cracking tube. A method of use, for example, wherein the fluid flows upward in the cracking tube by introducing the raw material mixed gas in reverse from the lower side of the cracking tube, may heavily foul inside of the cracking tube, resulting in clogging of the tube within a short period of time and a stop of operation of the apparatus.

In an apparatus in which a wave-like tube with up-and-down curving is transversely arranged, the fluid in the tube repeats up-and-down. This is undesirable from the same reason as above. That is, while the fluid in the tube is in the upward direction, heavy components contained in the crude dicyclopentadiene or by-produced during the cracking reaction may stick to the cracking tube internal wall and may become hard to be exhausted to the outside of the tube, residing at the same place for a long period of time while exposed to a high temperature, causing them to further polymerize and, at the same time, resulting in production of carbonized materials.

In this manner, according to the present invention, by the use of a cracking tube arrangement and a fluid flow system so as to constantly maintain the flow of the fluid downward, substances stuck to the internal wall of the tube are quickly expelled to the outside of the system, thus keeping the inside of the cracking tube free from fouling and ensuring a long-term stable operation. The time required for the crude dicyclopentadiene to be cracked in the thermal cracking tube (residence time) is 0.3–5 seconds on the basis of the raw material gas, with preferable range being 0.5–3 seconds. A sufficient cracking rate cannot be obtained with a residence time shorter than this range. A longer residence time is not desirable, because fouling of cracking tube due to polymers apt to occur. Although there are no specific restrictions as to the reaction pressure, a lower pressure is generally preferable from the aspect of accelerating the cracking reaction in the system, i.e., cracking tube or tubes, and of suppressing the formation of polymers. Generally, the pressure in the system, i.e., cracking tube or tubes, is in the range of 0–5 $Kg/cm^2$. G, and preferably 0–3 $Kg/cm^2$. G.

The gas taken out from the thermal cracking tube is a mixed gas comprising light components of which the major component is cyclopentadiene, heavy components such as dicyclopentadiene not decomposed, codimer, polymerized oils, and the like, and steam. This mixed gas is fed to the next liquefaction-separation step [D]. The liquefaction-separation step [D] is a step for removing heavy components with a boiling point higher than that of cyclopentadiene, including water, in order to selectively separate cyclopentadiene. As a method of separation, a partial condenser maintained at a temperature in the range of 45°–95° C., preferably 50–60° C., at which cyclopentadiene with a boiling point of 41° C. does not condense and steam condenses, may be used, or a simple distillation column, can be used to separate the heavy components as liquefied materials. In order to increase the yield of cyclopentadiene when the feed passes through this step, a precaution must be taken to suppress liquefaction of cyclopentadiene as small as possible so that cyclopentadiene may not be captured in this partial condenser.

The gas sent out from the partial condenser is substantially cyclopentadiene and contains a slight amount of light hydrocarbons such as isoprene, piperylene, and the like, and codimers, as well as several % by weight of water. Cyclopentadiene content of hydrocarbon gases excluding water is 80–99% by weight. The gas is cooled and totally condensed to recover liquefied cyclopentadiene. After removal of water, liquefied cyclopentadiene is sent to the redimerization step [E].

The conditions of the re-dimerization step [E] are almost the same as those of dimerization step [A]; cyclopentadiene is selectively dimerized here into dicyclopentadiene. Since the dimerized fraction contains 2–3% by weight of unreacted cyclopentadiene, it contains 77–96% by weight of dicyclopentadiene in which small amounts of light hydrocarbons and water accompanied from step [D], and heavy components such as a small amount of codimers and tricyclopentadiene, by-produced again in the re-dimerization step, and the like. In this and following steps, an antioxidant (BHT, etc.) may be added in order to suppress formation of oxidation products of dicyclopentadiene and the like; the addition of antioxidants does not specifically interfere the practice of the present invention.

After the re-dimerization, in order to obtain high purity dicyclopentadiene by removing a slight amount of impurities, said fraction is first introduced to light fraction removing step [F] using a vacuum distillation column, wherein light hydrocarbons and water are removed by distillation from the top of the distillation column. In this instance, from the aspect of the purity of dicyclopentadiene which is the target product of the present invention, it is desirable to remove some amount of dicyclopentadiene along with the small amount of light components, although some decrease in the yield of dicyclopentadiene is encountered. A preferable total amount to be distilled off from the top of the distillation column is, therefore, 5–25% by weight of the feed to this step [F]. The distillate from the top of the column usually contains a considerable amount of dicyclopentadiene and cyclopentadiene. Accordingly, it goes without saying that the recovery rate of high purity dicyclopentadiene of the present invention can be increased by recycling this fraction to the step [B] or an upstream side thereof. However, if desired, this fraction from the top of the column in step [F] may be directed to other use, e.g., it can be used as a raw material for manufacturing conventional cyclopentadiene-type petroleum resins, without recycling in the process of the present invention. When this fraction from the top of the column is recycled in the process of the present invention, it is usually returned to the outlet stream of dimerization step [A]; however, if desired, it can be returned to the feed to the dimerization step [A]. An amount corresponding to about one half or more of dicyclopentadiene and cyclopentadiene contained in the fraction obtained from the top of the column in step [F] contributes to the increase in the yield of high purity dicyclopentadiene by this recycling. Light components contained in the fraction from the top of the column in step [F] can be removed in concentration step [B], even though this recycling is carried out. Therefore, the purity of the target product, i.e., dicyclopentadiene, is not affected by the recycling.

Substances from the bottom of the column is fed to next vacuum distillation step [G], wherein most part of dicyclopentadiene is distilled out from the top of the column, thus affording high purity dicyclopentadiene with a purity of 97.0% by weight or more. By the process of the present invention, high purity dicyclopentadiene with purity of about 99.5% by weight or more can easily be prepared without any difficulty. While, from the bottom of the column, some amount of dicyclopentadiene is removed along with a slight amount of heavy components. The reason to do so is the same as in step [F].

Distillation conditions in both steps [F] and [G] are selected from the range, usually, of the column bottom temperature of 80°–120° C., and pressure of 5–200 Torr depending on the purpose of each step.

Furthermore, since a major portion of the column bottom fraction from step [G] is dicyclopentadiene, with the remaining portion being a small amount of heavy components which can be readily removed, the fraction is returned to aforementioned vapor-phase thermal cracking step [C] or its upstream side. It may be returned directly to the vapor-phase thermal cracking apparatus, but preferably be returned to the crude dicyclopentadiene with dicyclopentadiene content of about 70% by weight or more which is obtained from concentration step [B]. When the distillation procedure in the presence of water and/or steam is carried out prior to the vapor-phase thermal cracking of step [C], it is especially preferable that the column bottom fraction from step [G] be mixed with the raw material which is to be distilled in the presence of water and/or steam, i.e., crude dicyclopentadiene. The purity of the target high purity dicyclopentadiene is not lowered by this recycling, because the heavy components in the column bottom fraction of step [G] can easily be removed by the azeotropic or steam distillation which is carried out prior to step [C] or by the treatment in the next step [D]. Introducing this column bottom fraction to other steps of reuse by recycling may lower the yield of high purity dicyclopentadiene or may reduce its purity. Such methods, thus, are not preferable as a process for manufacturing a raw material for RIM.

High purity dicyclopentadiene suitable for use as raw material for RIM can be obtained in a high yield by the present invention. In addition, long-term continuous operation of the manufacturing unit is possible.

As mentioned above, a stable, long-term continuous operation of a dicyclopentadiene cracking unit is possible according to the present invention by merely controlling the direction of the fluid-flow in the cracking unit. An inexpensive manufacture of high purity dicyclopentadiene suitable for use as a raw material of RIM is possible in an industrial scale by the use of the process for the vapor-phase thermal cracking of dicyclopentadiene mentioned in preceding sentence.

In general, a further stable, long-term continuous operation is possible when crude dicyclopentadiene is supplied to the cracking unit as a mixed fraction with water by an azeotropic or a steam distillation.

DESCRIPTION OF THE PREFERRED EMBODIMENTS

The process of the present invention is hereinafter described in more detail by way of Examples, which are not limitative of the present invention.

EXAMPLE 1

FIG. 1 shows an example of steps of the vapor-phase thermal cracking of dicyclopentadiene and the liquefaction-separation of cyclopentadiene.

Cracking tube 2 is a stainless tube with an internal diamer of 10 mm and a length of 1,000 mm, which is vertically installed and externally heated by heater 3 to an average cracking temperature of 350° C. The heater used in this example is an electric heater.

The $C_5$ fraction with a composition shown in Table 1 was used as the starting raw material.

TABLE 1

| Composition | wt % |
|---|---|
| $C_3 + C_4$ | 2.0 |
| $C_5$ paraffin | 41.0 |
| $C_5$ olefin | 13.0 |

TABLE 1-continued

| Composition | wt % |
|---|---|
| Isoprene | 12.0 |
| Piperylene | 7.5 |
| Cyclopentene | 3.0 |
| Cyclopentadiene | 14.0 |
| Dicyclopentadiene | 2.0 |
| $C_6 + C_7^+$ | 5.5 |

The starting raw material, i.e., the $C_5$ fraction with the composition shown above, was dimerized and distilled to prepare crude dicyclopentadiene with a concentration of about 90% by weight.

The crude dicyclopentadiene in an amount of 450 g (dicyclopentadiene: 405 g, 307 mol) per hour and superheated steam in an amount of 45 g (2.5 mol) per hour were supplied as a mixture. After heating to 100°-200° C. in preheater 1, the mixture was fed to the upper part of the cracking tube 2 and allowed to stay in cracking tube 2 for 1.0 second calculated on the basis of the raw material mixed gas at a temperature of 350° C. under the atmospheric pressure. After that, cracked gas and steam were drawn out from a lower part of cracking tube 2 and fed to partial condenser 4 which was maintained at a temperature of 50° C., to remove most part of uncracked heavy components and water. In addition, cracked gas which was substantially cyclopentadiene was introduced to and liquefied in total condenser 5 which was kept at a temperature of 0° C.

Composition analysis made on the cracked gas revealed that the rate of cracking was 90% based on dicyclopentadiene in the crude raw material and, even though cyclopentadiene was partially condensed in the partial condenser 4, the yield of cyclopentadiene in total condenser 5 was 315 g per hour (recovery rate: 78%).

The cyclopentadiene product constantly kept the purity of 98% by weight or more and water content of 1% by weight or less, and after a 720 hour continuous operation, the inside of the thermal cracking tube was fouled only very slightly. The degree of fouling in the cracking tube was measured by the use of a differential manometer. After 720 hours continuous operation, the pressure loss found between the inlet and the outlet of the cracking tube was only 0.01 Kg/cm² which was almost the same value as measured before the operation. A longer continuous operation was judged to be possible.

EXAMPLE 2

Figure 2:
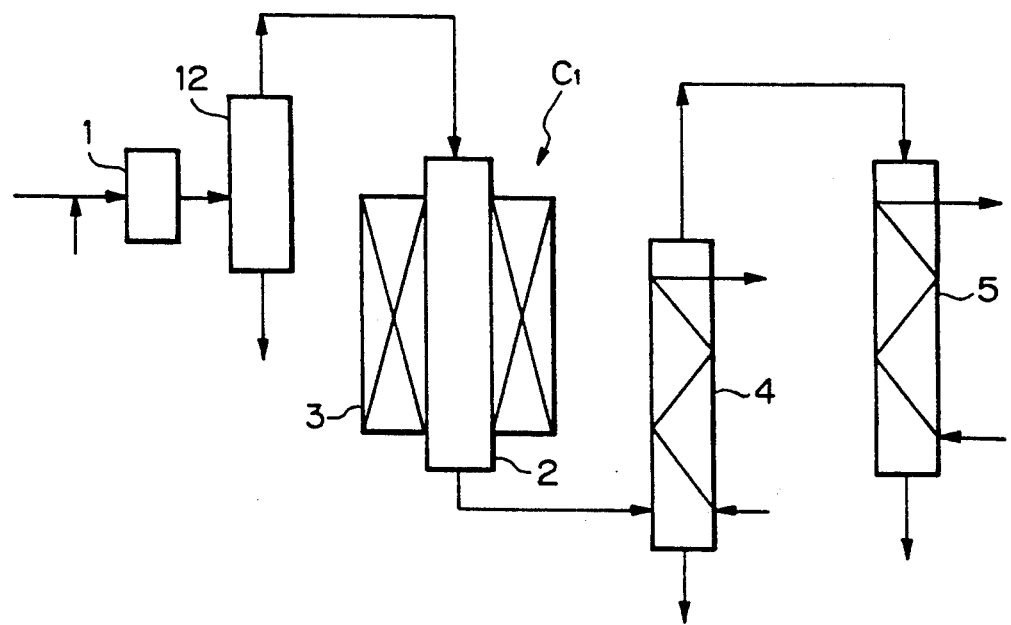
FIG. 2 shows another example of vapor-phase thermal cracking step of dicyclopentadiene and liquefaction separation step of cyclopentadiene according to the present invention.

FIG. 2 shows an example of the vapor-phase thermal cracking step of dicyclopentadiene and the liquefaction-separation step of cyclopentadiene, wherein the azeotropic or steam distillation is carried out in advance of the vapor-phase thermal cracking step.

Cracking tube 2 used was a stainless tube with an internal diameter of 10 mm and a length of 1,000 mm, which was vertically installed and externally heated by heater 3 to an average cracking temperature of 350° C. The heater used in this example was an electric heater.

The $C_5$ fraction with a composition shown in Table 1 was dimerized and distilled to prepare crude dicyclopentadiene with a concentration of about 90% by weight.

The crude dicyclopentadiene in an amount of 170 g (dicyclopentadiene: 153 g) per hour and hot water in an amount of 200 g per hour were supplied as a mixture. After heating to 100°-200° C. in preheater 1, the mixture was fed to distillation column 12, wherein the mixture was distilled under atmospheric pressure and a column top temperature of about 100°-110° C., thereby obtained a dicycloentadiene-water mixture containing a slight amount of light components and codimer from the top of the column. In this instance, from the bottom of the column, surplus water was removed in a rate of 6 g per hour and a major part of heavy components was removed in a rate of 9 g per hour. Next, said mixed fraction (the raw material mixed gas) obtained from the top of the column was introduced as a vapor into cracking tube 2 from the upper portion.

After having been allowed to stay in cracking tube 2 for 0.5 second calculated on the basis of the raw material mixed gas at a temperature of 350° C. under the atmospheric pressure, the cracked gas and steam were drawn out from a lower part of cracking tube 2 and fed to partial condenser 4 which was maintained at a temperature of 50° C., to remove most part of uncracked heavy components and water. Then, cracked gas which was substantially cyclopentadiene was introduced to and liquefied in total condenser 5 which was kept at a temperature of 0° C.

Composition analysis made on the cracked gas revealed that the rate of cracking was 90% based on dicyclopentadiene in the crude raw material and, even though cyclopentadiene was partially condensed in the partial condenser 4, the yield of cyclopentadiene in total condenser 5 was 119 g per hour (recovery rate: 78%).

The cyclopentadiene product constantly kept the purity of 98% by weight or more and water content of 1% by weight or less, and after a 720 hour continuous operation, fouling of the inside of the thermal cracking tube was less than in Example 1. The degree of fouling in the cracking tube was measured by the use of a differential manometer. After 720 hours continuous operation, the pressure loss found between the inlet and the outlet of the cracking tube was only 0.01 Kg/cm$^2$ which was almost the same value as measured before the operation. A continuous operation longer than in Example 1 was judged to be possible.

EXAMPLE 3

This example shows a conventional process and is not within the scope of the present invention.

The same procedures as in Example 1 were carried out, except that the raw material mixed gas was introduced from lower part of cracking tube 2. As a result, even though the same experimental values as in Example 1 were obtained with respect to the cracking rate of dicyclopentadiene, the yield of cyclopentadiene, and its purity, fouling of the thermal cracking tube was so heavy that the tube clogged in about 240 hours, forcing the operation to suspend. The pressure loss measured after the termination of the operation reached almost 1 Kg/cm$^2$. Since cleaning of the cracking tube was conducted by thermal decoking procedure by using a mixture of air and steam, the position where the clogging occurred was not measured.

EXAMPLE 4

Figure 3:
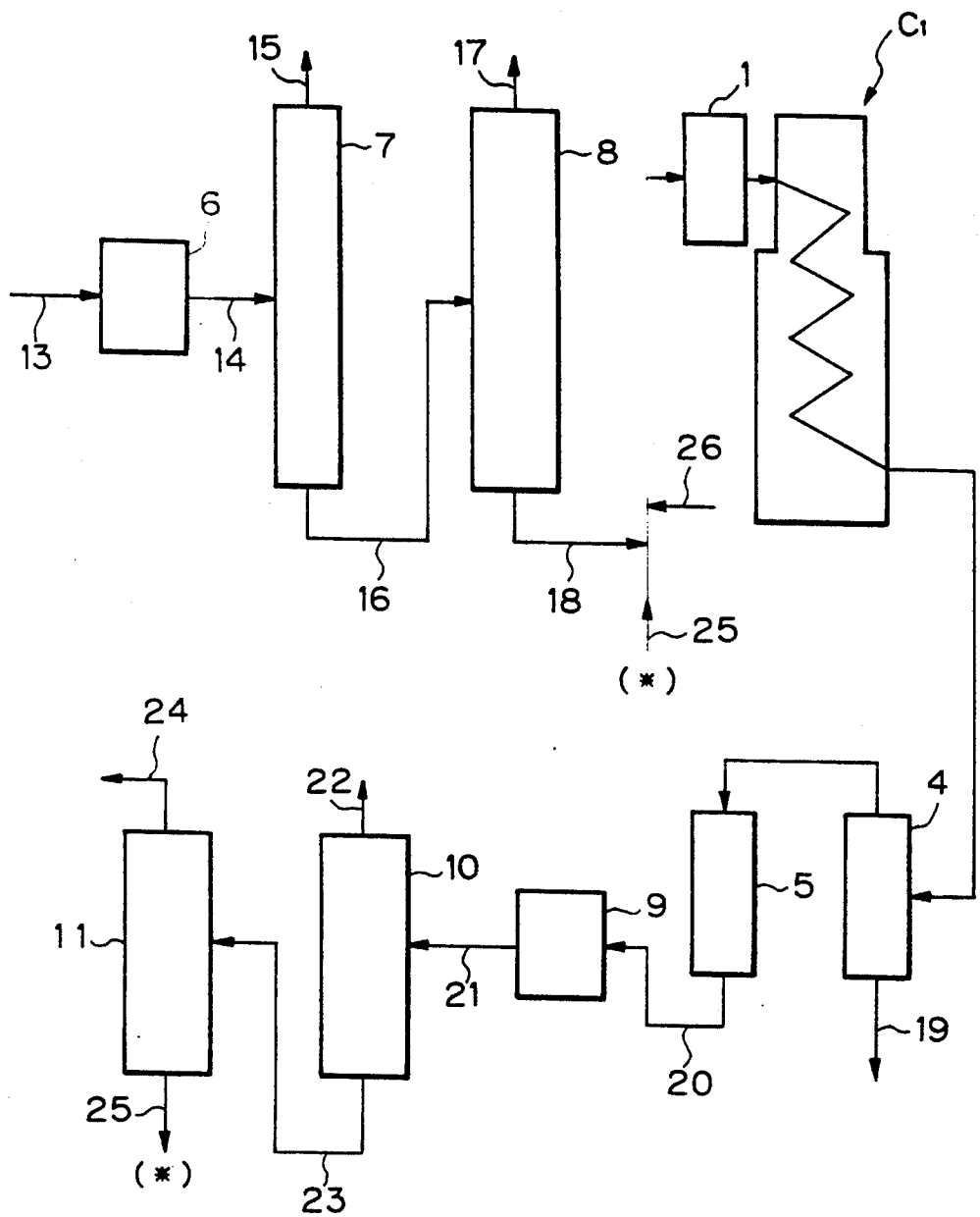
FIG. 3 a simplified explanatory flow diagram of an example of the access for manufacturing high purity dicyclopentadiene according to the present invention.

FIG. 3 is a simplified explanatory flow diagram of an example of the process for the manufacture of high purity dicyclopentadiene of the present invention. An experiment was carried out according to this flow. Since this experiment was continuously carried out, the weight of each fraction herein is designated in the weight per hour. "Parts" means parts by weight. The results of composition analysis on each fraction in the steps illustrated herein are shown in Table 2.

The C$_5$ fraction with a composition shown in Table 1 was supplied to dimerization vessel 6 via conduit 13 at a rate of 1,000 parts per hour to dimerize cyclopentadiene in the fraction into dicyclopentadiene under the reaction conditions: at a temperature of 90° C. and 4 hours of residence time. The conversion rate of cyclopentadiene to dicyclopentadiene was about 90%.

The fraction drawn out via conduit 14 from the dimerization vessel was sent to the next concentration step [B], wherein the unreacted C$_5$ fraction were removed. Concentration of dicyclopentadiene was carried out in two steps. First, the feed was introduced into an atmospheric distillation column with 10 theoretical plates, operated at a bottom temperature of 120° C. and a reflux ratio of 0.5, while distilling out 800 parts of unreacted C$_5$ fraction from the top of the column via conduit 15 and drawing 200 parts of dicyclopentadiene with a concentration of about 70% by weight from the bottom of the column via conduit 16. The fraction drawn out from the bottom was fed to another vacuum distillation column 8 in order to further concentrate dicyclopentadiene.

The distillation column 8 had 10 theoretical plates and was operated at a column bottom temperature of 120° C., pressure of 35 Torr, and a reflux ratio of 0.5, and from the top thereof 50 parts of a fraction mainly consisting of unreacted C$_5$ fraction was distilled off and drawn via conduit 17 and from the bottom 150 parts of crude dicyclopentadiene with a concentration of about 90% by weight was recovered via conduit 18. The unreacted C$_5$ fraction recovered in this step [C], i.e., from the tops of distillation columns 7 and 8, contained useful components such as isoprene, piperylene, and the like so that it could be used as a raw material for manufacturing petroleum resins or the like.

Next, the crude dicyclopentadiene was introduced into thermal cracking unit [C1] via a preheater 1. The thermal cracking unit [C1] comprised of a spiral metallic cracking tube which was vertically installed and externally heated by combustion gas. The preheater and the thermal cracking unit used in this example was integrally manufactured, although the appended drawing indicates them separately for the convenience of illustration. 150 Parts of the above crude dicyclopentadiene and 15 parts of superheated steam, which was supplied via conduit 26, were mixed (molar ratio: 136/1) and supplied to the preheater and introduced into the upper part of the cracking tube. The unit was operated at an average cracking temperature in the cracking tube of 350° C. and the residence time based on the raw material mixed gas of 1.0 second, with the flow of fluid being constantly maintained downward.

The cracked gas drawn from the lower part of the cracking tube was sent to partial condenser 4 which was maintained at 60° C. and, wherein 30 parts of a mixture of all uncracked components and thermally polymerized products with boiling points higher than cyclopentadiene and 13 parts of water representing almost all of the water in the system were liquefied and separated for removal via conduit 19. 15 Parts of cyclopentadiene which was the target compound in this liquefaction-separation step [D] was also liquefied together because of the proximity in vapor pressures of cyclopentadiene and impurities. The liquefaction of such a small amount of cyclopentadiene was inevitable so as to improve the purity of cyclopentadiene which was the target product in this step, i.e., the liquefaction-separation step [D]. The cracking rate based on dicyclopentadiene, including such cyclopentadiene which was liquefied in the partial condenser 4, reached 90%. Here 15 parts of the liquefied cyclopentadiene was also removed from conduit 19.

The cracked gas passed through partial condenser 4 was liquefied in the total condenser 5 kept at 20° C. to obtain 105 parts of cyclopentadiene with a purity of about 98% and 2 parts of water.

Water separated in the lower part of the liquid layer, although not indicated in the drawing, was discharged as a drain. 105 Parts of the liquefied cyclopentadiene was introduced into re-dimerization vessel 9 via conduit 20, and the dimerization reaction into dicyclopentadiene was again carried out at a temperature of 90° C. for 4 hours. The conversion rate of from cyclopentadiene to dicyclopentadiene was about 97% and the dicyclopentadiene obtained had a purity of about 96% due to a small amount of cyclopentadiene remaining as unreacted.

This fraction which was substantially dicyclopentadiene was sent to light component removing column 10 via conduit 21 in order to remove a slight amount of remaining light components. Light component removing column 10 had 20 theoretical plates and was operated under reduced pressure of 100 Torr, at a temperature of 110° C., and a reflux ratio of 2, and from the top thereof 15 parts of a mixture of light components and dicyclopentadiene was distilled out via conduit 22 and form the bottom 90 parts of a dicyclopentadiene fraction with a higher concentration was drawn via conduit 23.

Even though the bottom fraction was dicyclopentadiene with a sufficiently high concentration, it still contained a very small amount of heavy components such as codimer so that it was sent to the next dicyclopentadiene fractionation column 11. The fractionation column had 20 theoretical plates and was operated under reduced pressure of 15 Torr, at a temperature of 100° C., and a reflux ratio of 1, and from the top thereof 80 parts of the target dicyclopentadiene was continuously recovered via conduit 24 and from the bottom 10 parts of dicyclopentadiene which contained a slight amount of high boiling point materials was drawn out via conduit 25.

Dicyclopentadiene obtained from the top of the column had a purity of 99.8% by weight and the polymerization was confirmed to proceed well in the polymerization activity test for the RIM.

A major part of the fraction from the column bottom was dicyclopentadiene with slight amount of heavy components remaining therein. It was reusable as a cracking raw material, and was thus introduced into the thermal cracking unit, [C1] after mixed with crude dicyclopentadiene.

The yield of high purity dicyclopentadiene increased to 85 parts per hour by the recycling of the bottom fraction of the fractionation column 11. By the recycling operation, a decrease in the purity was not seen at all.

TABLE 2

| Conduit No. | 14 | 16 | 18 | 20 | 21 | 22 | 24 | 25 |
|---|---|---|---|---|---|---|---|---|
| Compositions (wt %) | | | | | | | | |
| C$_3$ + C$_4$ | 2.0 | — | — | — | — | — | — | — |
| C$_5$ | 75.4 | 9.5 | 0.6 | 1.1 | 1.0 | 6.5 | 0.1 | — |
| CPD[1] | 1.2 | 0.5 | — | 98.7 | 2.2 | 15.4 | — | — |
| C$_6$ + C$_7$ | 5.5 | 10.4 | 0.1 | 0.1 | 0.1 | 0.7 | — | — |
| PN[2] | 0.6 | 3.1 | 2.8 | — | 0.1 | 0.4 | 0.05 | — |
| DCPD[3] | 14.2 | 70.5 | 88.8 | 0.1 | 96.0 | 76.9 | 99.8 | 94.9 |
| Codimer | 0.3 | 1.8 | 2.5 | — | 0.2 | 0.1 | 0.05 | 1.0 |
| TCPD[4] | 0.8 | 4.2 | 5.2 | — | 0.4 | — | — | 4.1 |

[1] Cyclopentadiene;
[2] Propenylnorbornene;
[3] Dicyclopentadiene;
[4] Tricyclopentadiene

EXAMPLE 5

Figure 4:
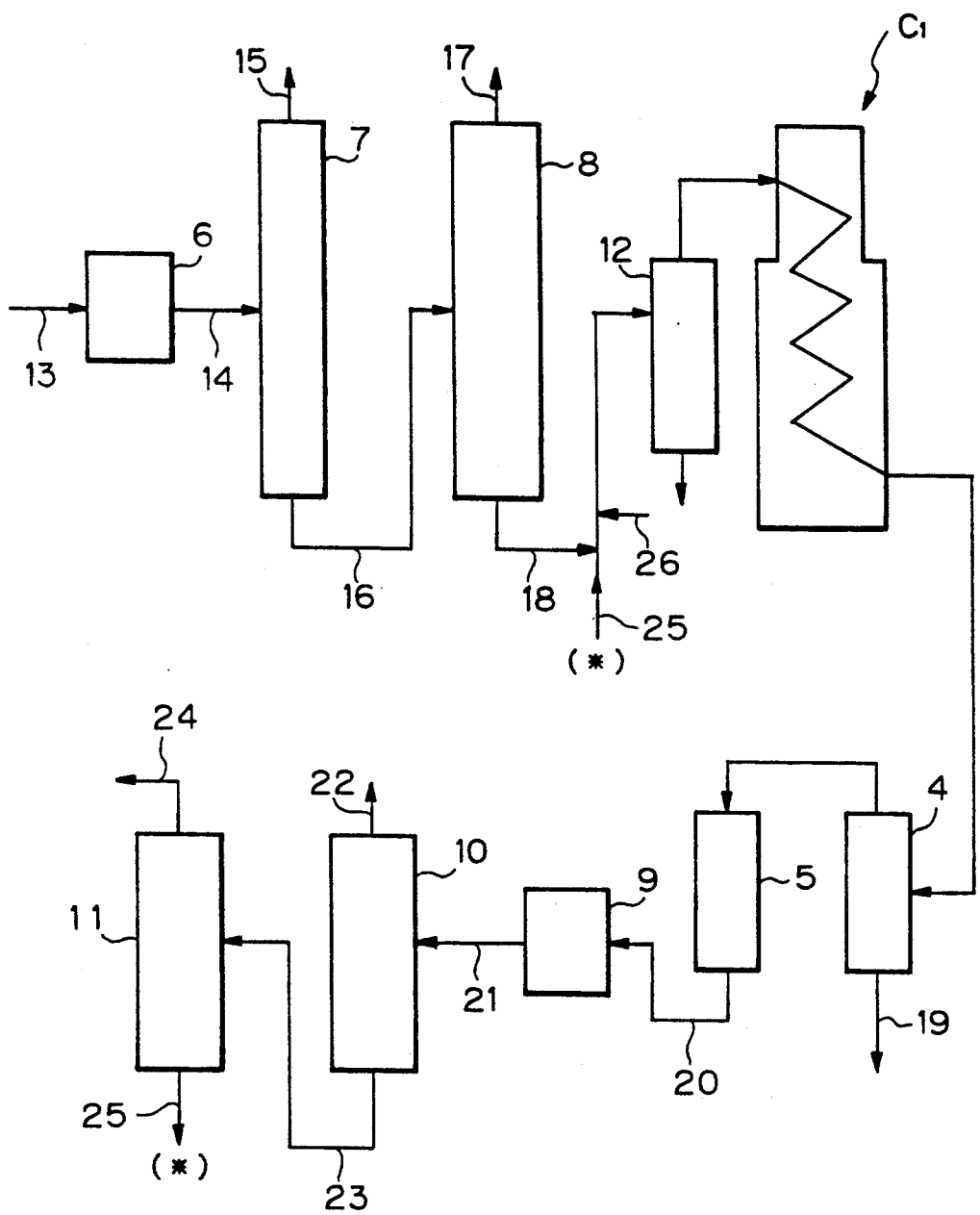
FIG. 4 a simplified explanatory flow diagram of another example of the process for manufacturing high purity dicyclopentadiene according to the present invention.

FIG. 4 is a simplified explanatory flow diagram of an example of the process for the manufacture of high purity dicyclopentadiene of the present invention. The experiment was carried out according to this flow. Since this experiment was continuously carried out, the weight of each fraction herein is designated in the weight per hour. "Parts" means parts by weight. The results of composition analysis on each fraction in steps illustrated herein are shown in Table 3.

The C$_5$ fraction with a composition shown in Table 1 was supplied to dimerization vessel 6 via conduit 13 at a rate of 1,000 parts per hour to dimerize cyclopentadiene into dicyclopentadiene under the reaction conditions of temperature of 90° C. and residence time of 4 hours. The conversion rate of cyclopentadiene into dicyclopentadiene was about 90%.

The fraction drawn out via conduit 14 from the dimerization vessel was sent to the next concentration step [B], wherein the unreacted C$_5$ fraction were removed. Concentration of dicyclopentadiene was carried out in two steps. First, the feed was introduced into atmospheric distillation column 7 with 10 theoretical plates, operated at a bottom temperature of 120° C. and a reflux ratio of 0.5, while distilling out 800 parts of unreacted C$_5$ fraction from the top of the column via conduit 15 and drawing 200 parts of dicyclopentadiene with a concentration of about 70% by weight from the bottom of the column via conduit 16. The fraction drawn from the bottom was fed to another vacuum distillation column 8 in order to further concentrate dicyclopentadiene.

The distillation column 8 had 10 theoretical plates and was operated at a column bottom temperature of 120° C., pressure of 35 Torr, and a reflux ratio of 0.5, and from the top thereof 50 parts of a fraction mainly consisting of unreacted C$_5$ fraction was distilled off and drawn via conduit 17 and from the bottom 150 parts of crude dicyclopentadiene with a concentration of about 90% by weight was recovered via conduit 18. The unreacted C$_5$ fraction recovered in this step [B], i.e., from the tops of distillation columns 7 and 8, contained useful components such as isoprene, piperylene, and the like so that it could be used as a raw material for manufacturing petroleum resins and the like.

Next, 150 parts of the crude dicyclopentadiene was introduced into distillation column 12 after mixing with 180 parts of superheated steam which was supplied via conduit 26. From the top of the column a slight amount of light components and codimer were distilled together with a mixture of dicyclopentadiene and water at a temperature of about 100° C., while from the bottom of the column 10 parts of a surplus amount of water and 8 parts of heavy components were discharged. Since the heat required for the distillation was sufficiently supplied by the superheated steam in this example, preheater 1 used in Examples 1-4 was omitted.

The mixed fraction from the top of the distillation column 12 was sent to thermal cracking unit [C1] as a vapor mixture. The thermal cracking unit [C1] was composed of a spiral metallic cracking tube which was vertically installed and externally heated by combustion gas. The above raw material mixed gas was introduced into the inlet at the upper part of the cracking tube. The average cracking temperature in the cracking tube was 350° C. and the residence time based on the raw material mixed gas was about 0.5 second, with the flow of fluid being constantly maintained downward.

The cracked gas drawn out from the lower part of the cracking tube was sent to partial condenser 4 maintained at 60° C., wherein 22 parts of a mixture of all uncracked components and thermal polymerization products with a boiling point higher than cyclopentadiene and 167 parts of water representing almost all of the water in the system were liquefied and separated for removal via conduit 19. 20 Parts of cyclopentadiene which was the target compound of this step, i.e., liquefaction-separation step [D], was also liquefied together because of the proximity in vapor pressures of cyclopentadiene and impurities. The liquefaction of such a small amount of cyclopentadiene was inevitable so as to improve the purity of cyclopentadiene which was the target product in this step, i.e., the liquefaction-separation step [D]. The cracking rate based dicyclopentadiene, including such cyclopentadiene liquefied in this step [D], reached 90%. Here, 20 parts of the liquefied cyclopentadiene was also removed via conduit 19.

The cracked gas passed through partial condenser 4 was liquefied in the total condenser 5 kept at 20° C. to obtain 100 parts of cyclopentadiene with a purity of above 98% and 3 parts of water.

Water separated in the lower part of the liquid layer, although not indicated in the drawing, was discharged as a drain. 100 Parts of the liquefied cyclopentadiene was introduced into re-dimerization vessel 9 via conduit 20, and the dimerization reaction into dicyclopentadiene was carried out at a temperature of 90° C. for 4 hours.

The conversion rate of from cyclopentadiene to dicyclopentadiene was 97% and the dicyclopentadiene obtained had a purity of about 96% due to a small amount of cyclopentadiene remaining unreacted.

This fraction which was substantially dicyclopentadiene was sent to light component removing column 10 via conduit 21 in order to remove a slight amount of remaining light components and water. The light component removing column 10 had 20 theoretical plates and was operated under reduced pressure of 100 Torr, at a temperature of 110° C., and a reflux ratio of 2, and from the top thereof 15 parts of a mixture of light components, water, and dicyclopentadiene was distilled off via conduit 22 and from the bottom 85 parts of a dicyclopentadiene fraction with a higher concentration was recovered via conduit 23.

Even though the bottom fraction was dicyclopentadiene with sufficiently high concentration, it still contained a very small amount of heavy components such as codimer and the like, so that it was sent to the next dicyclopentadiene fractionation column 11. The fractionation column 11 had 20 theoretical plates and was operated under reduced pressure of 15 Torr, at a temperature of 100° C., and reflux ratio of 1, and from the top thereof 75 parts of the target dicyclopentadiene was continuously obtained via conduit 24 and from the bottom 10 parts of dicyclopentadiene which contained a slight amount of high boiling point materials was drawn out via conduit 25.

Dicyclopentadiene obtained from the top of the column had a purity of 99.7% by weight and the polymerization was confirmed to proceed well in the polymerization activity test for the RIM.

A major part of the fraction from the column bottom was dicyclopentadiene with a slight amount of heavy components remaining therein. Therefore, it was reusable as a cracking raw material, and was thus introduced into distillation column 12 after mixed with crude dicylopentadiene.

The yield of high purity dicyclopentadiene increased to 80 parts per hour by the recycling of the bottom fraction of the fractionation column 11. By the recycling operation, a decrease in the purity was not seen at all.

TABLE 3

| Conduit No. | 14 | 16 | 18 | 20 | 21 | 22 | 24 | 25 |
|---|---|---|---|---|---|---|---|---|
| Compositions (wt %) | | | | | | | | |
| $C_3 + C_4$ | 2.0 | — | — | — | — | — | — | — |
| $C_5$ | 75.4 | 9.8 | 0.6 | 1.9 | 1.3 | 8.2 | 0.1 | — |
| CPD[1] | 1.3 | 1.1 | — | 97.9 | 1.8 | 12.0 | — | — |
| $C_6 + C_7$ | 5.5 | 11.1 | 0.1 | 0.1 | 0.1 | 0.7 | — | — |
| PN[2] | 0.6 | 2.8 | 3.1 | — | 0.2 | 0.8 | 0.1 | — |
| DCPD[3] | 14.0 | 68.9 | 88.4 | 0.1 | 95.5 | 76.7 | 99.7 | 92.6 |
| Codimer | 0.4 | 2.0 | 2.1 | — | 0.7 | 1.6 | 0.1 | 1.2 |
| TCPD[4] | 0.8 | 4.3 | 5.7 | — | 0.5 | — | — | 6.2 |

[1] Cyclopentadiene;
[2] Propenylnorbornene;
[3] Dicyclopentadiene;
[4] Tricyclopentadiene

We claim:

1. A process for manufacturing high purity dicyclopentadiene from $C_5$ fractions obtained in thermal cracking of petroleum comprising the steps of:

A. heating a $C_5$ fraction to dimerize cyclopentadiene contained in said $C_5$ fraction;

B. distilling off unreacted $C_5$ components from the effluent of step A to obtain crude dicyclopentadiene having a dicyclopentadine concentration of 70% by weight or more;

C. thermally cracking, in a vapor-phase process, a mixture of said crude dicyclopentadiene and water and/or steam in a cracking tube or tubes under cracking conditions comprising a temperature ranging between about 250° C. and 450° C., wherein the mixing ratio of said crude dicyclopentadiene and said water and/or steam is between about 5 and 230 parts by weight of water and/or steam for each 100 parts by weight of said crude dicyclopentadiene, with the residence time of said mixture in said cracking tube or tubes being between about 0.3 and 5 seconds calculated as gaseous state of said mixture under the cracking conditions used and the direction of flow of said mixture passing through said cracking tube or tubes is constantly maintained downward;

D. cooling the effluent of step C to liquify water and heavy components contained in the effluent of step C, separating and removing the liquified water and heavy components from a gas consisting substantially of cyclopentadiene, further cooling the gas to liquify the cyclopentadiene and recovering the liquified cyclopentadiene;

E. redimerizing said cyclopentadiene obtained from step D;

F. distilling the effluent of step E to remove light components as overhead;

G. fractionating the bottom fraction of step F to recover purified dicyclopentadiene as the overhead fraction; and H. recycling the heavy fraction obtained as the bottom fraction of step G to said step C, to said step B, or to said step A.

2. The process defined in claim 1, wherein the purified dicyclopentadiene obtained from said step G has a dicyclopentadiene concentration of at least 97.0% by weight.

3. The process defined in claim 1, wherein said mixing ratio of said crude dicyclopentadiene and said water and/or steam is between about 50 and 230 parts by weight of water and/or steam for each 100 parts by weight of said crude dicyclopentadiene, said mixture of said crude dicyclopentadiene and said water and/or steam is distilled at a temperature which corresponds to 120° C. or below under atmospheric pressure to obtain a distillate comprising said crude dicyclopentadiene and said water and/or steam, the distillate is introduced into said step C, and the heavy fraction obtained as the bottom fraction of said step G is mixed with said crude dicyclopentadiene before being recycled to said step C.

4. The process defined in claim 3 wherein the purified dicyclopentadiene obtained from said step G has a dicyclopentadiene concentration of at least 97.0% by weight.

5. The process defined in claim 3, wherein the light components which are distilled out in said step F are recycled to said step B or to said step A.

6. The process defined in claim 1, wherein the light components which are distilled out in said step F are recycled to said step B or to said step A.

* * * * *